(12) United States Patent
Yamada et al.

(10) Patent No.: US 10,041,100 B2
(45) Date of Patent: Aug. 7, 2018

(54) METHOD OF PRODUCING SUGAR SOLUTION

(71) Applicant: Toray Industries, Inc., Tokyo (JP)

(72) Inventors: Chiaki Yamada, Kamakura (JP); Hiroyuki Kurihara, Kamakura (JP); Katsushige Yamada, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 14/765,416

(22) PCT Filed: Mar. 3, 2014

(86) PCT No.: PCT/JP2014/055244
§ 371 (c)(1),
(2) Date: Aug. 3, 2015

(87) PCT Pub. No.: WO2014/136711
PCT Pub. Date: Sep. 12, 2014

(65) Prior Publication Data
US 2015/0376669 A1 Dec. 31, 2015

(30) Foreign Application Priority Data

Mar. 4, 2013 (JP) ................. 2013-041700

(51) Int. Cl.
| | | |
|---|---|---|
| *C12P 19/14* | (2006.01) | |
| *C13K 1/02* | (2006.01) | |
| *C12P 19/04* | (2006.01) | |
| *B01D 61/14* | (2006.01) | |
| *C12P 19/02* | (2006.01) | |

(52) U.S. Cl.
CPC ............ *C12P 19/14* (2013.01); *B01D 61/145* (2013.01); *B01D 61/147* (2013.01); *C12P 19/02* (2013.01); *C12P 19/04* (2013.01); *C13K 1/02* (2013.01); *B01D 2311/25* (2013.01); *B01D 2311/2688* (2013.01); *C12P 2201/00* (2013.01); *C12P 2203/00* (2013.01)

(58) Field of Classification Search
CPC ..... B01D 61/14; C02F 1/441; C11D 3/38645; C12N 9/2437; C12Y 302/01004; C01D 1/00; D06M 16/003
See application file for complete search history.

(56) References Cited

U.S. PATENT DOCUMENTS

| | | |
|---|---|---|
| 2013/0203117 A1 | 8/2013 | Kurihara et al. |
| 2013/0266991 A1* | 10/2013 | Kanamori ............ C13K 13/002 435/99 |
| 2014/0287461 A1 | 9/2014 | Kurihara et al. |

FOREIGN PATENT DOCUMENTS

| | | |
|---|---|---|
| EP | 2 650 384 A1 | 12/2011 |
| JP | 2006-87319 A | 4/2006 |
| JP | 2011-223975 A | 11/2011 |
| JP | 2012-100617 A | 5/2012 |
| JP | 4947223 B1 | 6/2012 |
| WO | 2010/067785 A1 | 6/2010 |
| WO | 2011/115040 A1 | 9/2011 |
| WO | 2012/077697 A1 | 6/2012 |
| WO | WO2012077697 * 6/2012 ............... C13K 1/04 |

OTHER PUBLICATIONS

Otter et al. Elution of Trichoderma reesei cellulase from cellulose by pH adjustment with sodium hydroxide. Biotechnology Letters. 1984;6(6):369-374.*
Awg-Adeni et al. Recovery of glucose from residual starch of sago hampas for bioethanol production. BioMed Research International. 2013;1-8.*
Extended European Search Report dated Sep. 2, 2016, from corresponding EP Application No. 14759685.2.
Notification of Reasons for Refusal dated Nov. 16, 2017, of corresponding Japanese Application No. 2014-511650, along with an English translation.
European Communication dated Dec. 6, 2017, of corresponding European Application No. 14759685.2.

* cited by examiner

*Primary Examiner* — Lynn Y Fan
(74) *Attorney, Agent, or Firm* — DLA Piper LLP (US)

(57) ABSTRACT

A method of producing sugar solution by repeating a sugar solution production process includes steps (1) to (3), wherein a wash solution obtained in step (4) of washing a separation membrane after step (3) is used for step (1) of subsequent sugar solution production processes:
  step (1): preparing slurry of pretreated cellulose-containing biomass;
  step (2): hydrolyzing the slurry of pretreated cellulose-containing biomass in step (1) using cellulase from filamentous fungi; and
  step (3): subjecting the hydrolyzate of step (2) to solid-liquid separation into a solution component and a hydrolysis residue, filtering the solution component through an ultrafiltration membrane and recovering the cellulase from filamentous fungi as a non-permeate, and recovering the sugar solution as a permeate.

11 Claims, 1 Drawing Sheet

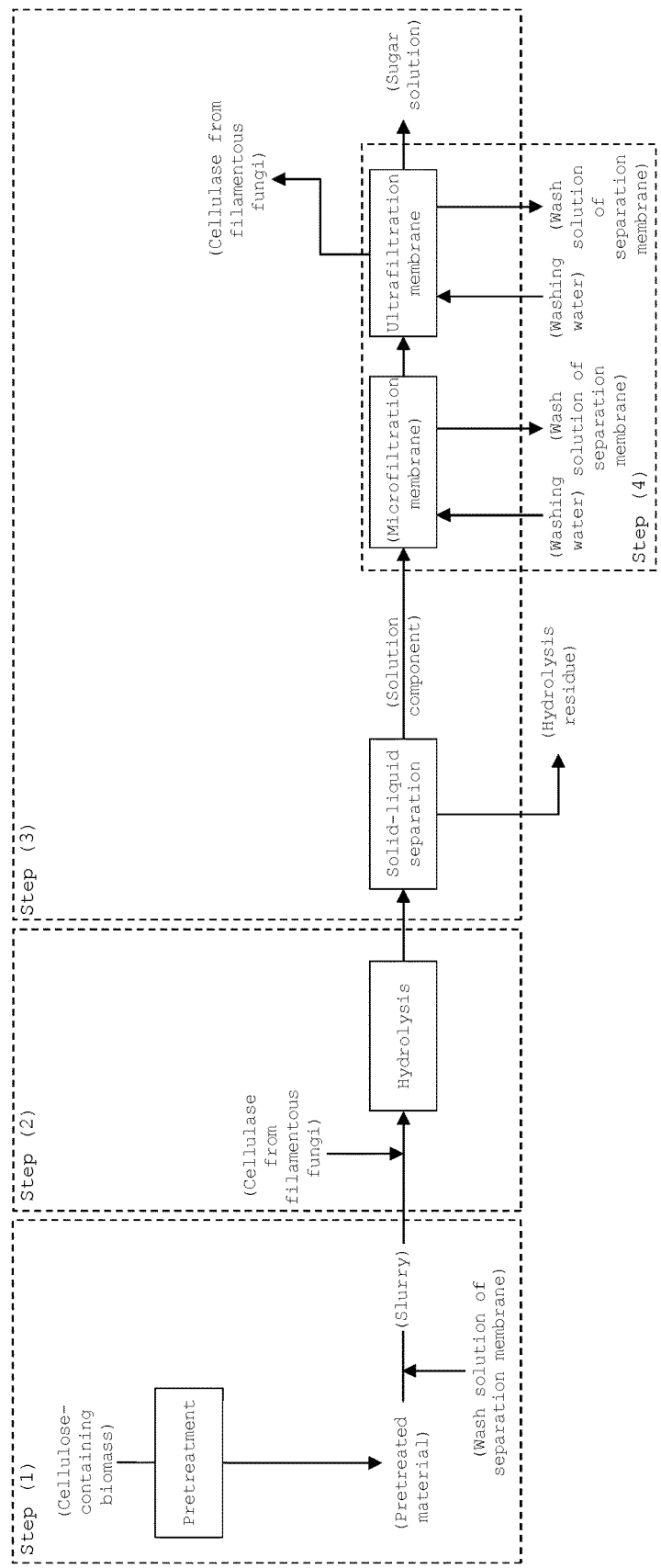

METHOD OF PRODUCING SUGAR SOLUTION

TECHNICAL FIELD

This disclosure relates to a method of producing a sugar solution from a cellulose-containing biomass.

BACKGROUND

In recent years, there have been widely studied a method of producing a sugar solution by hydrolysis of a cellulose-containing biomass using cellulase, of which energy consumption and environmental burdens are low. However, the greatest defect of the method of producing a sugar solution using cellulase is the point that the production cost of a sugar solution increases due to the high price of cellulase. Although there has been proposed a method of recovering and reusing cellulase used for hydrolysis to solve such a technical problem, it is a problem that reusability is low since cellulase strongly adsorbs the hydrolysis residue produced upon hydrolysis of the cellulose-containing biomass.

As a method of reducing adsorption of cellulase to the hydrolysis residue, a method of adjusting the electrical conductivity of the reaction liquid to 5 to 25 mS/cm by adding a water-soluble salt upon hydrolysis of a cellulose-containing biomass (JP 4947223 B1), a method of adding calcium carbonate particles at an amount of 1 to 10% by weight based on the weight of a solid of a cellulose-containing biomass (JP 2012-100617 A), and the like are known.

As described above, a wide variety of attempts to reduce the amount of use of cellulase by recovering and reusing cellulase used for hydrolysis of a cellulose-containing biomass are made. However, since cellulase strongly adsorbs the hydrolysis residue, the recovery rate is low, and the problem has not been solved yet. It could therefore be helpful to provide a method of producing a sugar solution, wherein cellulase can be recovered more efficiently than in a conventional method.

SUMMARY

We found that in a method of producing sugar solution by repeating sugar solution producing process using an ultrafiltration membrane and/or a microfiltration membrane, enzyme components of cellulase from filamentous fungi can be highly efficiently recovered by using a wash solution, obtained in a washing step of a separation membrane, to prepare the slurry of the pretreated cellulose-containing biomass in the subsequent processes.

We thus provide:

[1] a method of producing sugar solution by repeating a sugar solution production process comprising the following steps (1) to (3), wherein the wash solution obtained in step (4) of washing a separation membrane after step (3) is used for step (1) of subsequent sugar solution production processes:

step (1): preparing slurry of pretreated cellulose-containing biomass;
step (2): hydrolyzing the slurry of pretreated cellulase-containing biomass in step (1) using cellulase from filamentous fungi; and
step (3): subjecting the hydrolyzate of step (2) to solid-liquid separation into a solution component and a hydrolysis residue, and filtering the solution component through an ultrafiltration membrane and recovering the cellulase from filamentous fungi as a non-permeate, and recovering the sugar solution as a permeate;

[2] the method of producing sugar solution according to [1], wherein the permeate obtained by filtering the solution component in step (3) through a microfiltration membrane is filtered through an ultrafiltration membrane;

[3] the method of producing sugar solution according to [2], wherein the wash solution obtained by washing the ultrafiltration membrane and/or microfiltration membrane in step (4) is used in step (1) of the subsequent sugar solution production process;

[4] the method of producing sugar solution according to any of [1] to [3], wherein step (4) is washing with washing water containing an alkaline substance;

[5] the method of producing sugar solution according to any of [1] to [4], wherein the cellulase from filamentous fungi is from a microorganism of the genus *Trichoderma*;

[6] the method of producing sugar solution according to any of [1] to [5], wherein pretreatment of the cellulose-containing biomass in step (1) is dilute sulfuric acid treatment.

It is thus possible to suppress adsorption of cellulase from filamentous fungi to the hydrolysis residue of the cellulose-containing biomass. Specifically, the β-glucosidase, which plays an important role in the hydrolysis reaction, can be efficiently recovered and/or reused. As a result, the sugar solution production cost can be reduced.

BRIEF DESCRIPTION OF THE DRAWING

FIG. 1 shows a schematic drawing of an example of the method of preparing sugar solution.

DETAILED DESCRIPTION

Each step of examples of carrying out our methods will be hereinafter explained. In the method of producing sugar solution, steps (1) to (3) explained below and optionally step (4) are repeatedly carried out.

Step (1): Step of Preparing Slurry of Pretreated Cellulose-Containing Biomass

Cellulose-containing biomass includes herbaceous biomass such as bagasse, switchgrass, napier grass, erianthus, corn stover, beet pulp, a cottonseed hull, a palm empty fruit bunch, rice straw, wheat straw, bamboo and bamboo grass; or woody biomass such as a tree such as white birch and beech, and waste building materials. Since cellulose-containing biomass contains lignin which is an aromatic polymer, in addition to cellulose and hemicellulose, which are composed of sugar, hydrolysis efficiency by cellulase can be improved by subjecting the biomass to pretreatment. The method of pretreatment of cellulose-containing biomass includes dilute acid treatment, alkaline treatment, hydrothermal treatment, subcritical water treatment, micropulverization treatment and the like. Since reusability of the enzyme in the method of producing sugar solution is highest when a material treated with dilute sulfuric acid is used, a material treated with dilute sulfuric acid is preferably applied.

The solid concentration of the slurry of the pretreatment material is not specifically limited, but preferably 1 to 30% by weight. When the solid concentration is low, the concentration of sugar produced by hydrolysis may be low, and it may be difficult to utilize the product as a raw material for fermentation in some cases. On the other hand, when the concentration is too high, it may be difficult to handle the product in some cases.

The pH of the slurry is not specifically limited, but preferably 3.0 to 7.0, within which range cellulase from filamentous fungi can act well. To carry out a hydrolysis reaction efficiently with smaller amount of cellulase from filamentous fungi, the pH is more preferably pH 3.5 to 6.5, which is close to the optimum pH of cellulase from filamentous fungi, and further preferably pH 4.0 to 6.0. Since pH changes in the course of hydrolysis, it is preferable to add a buffer to the reaction solution or to carry out hydrolysis with keeping constant pH using an acid or an alkali.

Step (2): Step of Hydrolyzing the Slurry of the Pretreatment Product of Cellulose-Containing Biomass in Step (1) Using Cellulase from Filamentous Fungi Filamentous fungi used as an origin of cellulase include microorganisms of the genera *Trichoderma, Aspergillus, Cellulomonas, Chlostridium, Streptomyces, Humicola, Acremonium, Irpex, Mucor, Talaromyces* and the like. In addition, cellulase may be from a variant of which cellulase productivity is improved by subjecting such microorganisms to mutation treatment by a mutagen or ultraviolet irradiation and the like.

Among filamentous fungi, the genus *Trichoderma* can be preferably used since the genus *Trichoderma* produces an enzyme component having high specific activity in hydrolysis of cellulose in a large amount in the culture solution. A concrete example of cellulase from the genus *Trichoderma* includes cellulase from *Trichoderma reesei* QM 9414, *Trichoderma reesei* QM 9123, *Trichoderma reesei* Rut C-30, *Trichoderma reesei* PC 3-7, *Trichoderma reesei* CL-847, *Trichoderma reesei* MCG 77, *Trichoderma reesei* MCG 80 and *Trichoderma viride* QM 9123, and cellulase from *Trichoderma reesei* is more preferable among them.

Cellulase from filamentous fungi is an enzyme composition having an activity of producing a monosaccharide such as glucose and xylose by hydrolysis of cellulose and/or hemicellulose, and preferably comprises one or more kinds selected from the group consisting of cellobiohydrolase, endoglucanase, β-glucosidase, xylanase and β-xylosidase. For example, as an enzyme component of cellulase from *Trichoderma reesei*, cellobiohydrolase I, cellobiohydrolase II, endoglucanase I, endoglucanase III, β-glucosidase, xylanase, β-xylosidase and the like can be exemplified. Since efficient hydrolysis of cellulose and/or hemicellulose can be carried out by a concerted effect or a complementary effect of such plural enzyme components, such plural enzyme components are preferably used.

Cellobiohydrolase is a general term of enzymes which release cellobiose by hydrolysis of a cellulose chain, and an enzyme group belonging to cellobiohydrolase is described as EC number: EC 3.2.1.91. Cellobiohydrolase I starts a hydrolysis reaction from the reducing end of a cellulose chain, and cellobiohydrolase II starts a hydrolysis reaction from the non-reducing end.

Endoglucanase is a general term of enzymes characterized by starting hydrolysis from the middle of a cellulose chain, and an enzyme group belonging to endoglucanase is described as EC number: EC 3.2.1.4. Endoglucanase I is most expressed among endoglucanases produced from cellulase from *Trichoderma reesei*, and has wide substrate specificity. Endoglucanase III has characteristics of having no cellulose binding module (CBM) and having low molecular weight.

β-Glucosidase is a general term of enzymes characterized by acting on cellooligosaccharide or cellobiose, and an enzyme group belonging to β-glucosidase is described as EC number: EC 3.2.1.21.

Xylanase is a general term of enzymes characterized by acting on hemicellulose or especially on xylan, and an enzyme group belonging to xylanase is described as EC number: EC 3.2.1.8.

β-Xylosidase is a general term of enzymes characterized by acting on a xylooligosaccharide, and an enzyme group belonging to β-xylosidase is described as EC number: EC 3.2.1.37.

Such cellulase components can be separated by a known method such as gel filtration, ion exchange and two-dimensional electrophoresis, and identified by comparing the amino acid sequence of the separated component with a database. Known analytical methods such as N-terminal analysis, C-terminal analysis, and mass spectrometry can be used for the analysis of the amino acid sequence.

The enzyme activity of cellulase from filamentous fungi can be evaluated by polysaccharide hydrolysis activity such as Avicel degradation activity, carboxymethyl cellulose (CMC) degradation activity, cellobiose degradation activity, xylan degradation activity and mannan degradation activity. The main enzyme exhibiting Avicel degradation activity is cellobiohydrolase, having a characteristic of hydrolyzing from the cellulose terminal regions. The main enzyme exhibiting cellobiose degradation activity is β-glucosidase. The main enzyme involved in CMC degradation activity is cellobiohydrolase and endoglucanase. The main enzyme exhibiting xylan degradation activity is xylanase and β-xylosidase. The meaning of "main" herein expresses that most involvement thereof in degradation is known, and means that other enzyme components are involved in the degradation.

Since filamentous fungi produce cellulase in a culture solution, the culture solution can be directly used as a crude enzyme agent, or an enzyme group may be purified by a known method and formulated and the purified and formulated cellulase from filamentous fungi can be used as a mixture of cellulase from filamentous fungi. When the purified and formulated cellulase from filamentous fungi is used, a substance other than the enzyme such as a protease inhibitor, a dispersant, a dissolution accelerator and a stabilizer may be added and used. Among them, a crude enzyme product is preferably used. The crude enzyme product is derived from a culture supernatant wherein filamentous fungi were cultured in a medium prepared so that the filamentous fungi produce cellulase for an arbitrary period. The medium component to be used is not specifically limited, and a medium to which cellulose is added for enhancing production of cellulase can be generally used. As a crude enzyme product, a culture solution itself or a culture supernatant from which only the genus *Trichoderma* fungus body is removed is preferably used.

The weight ratio of each enzyme component in the crude enzyme product is not specifically limited. For example, a culture solution from *Trichoderma reesei* contains 50 to 95% by weight of cellobiohydrolase, and the residual components contain endoglucanase, β-glucosidase and the like. A microorganism of the genus *Trichoderma* produces a strong cellulase component in the culture solution. On the other hand, regarding β-glucosidase, since the microorganism retains a large part of β-glucosidase in the cell or in the cell surface layer, β-glucosidase activity is low in the culture solution. Thus, a heterogenous or homogenous β-glucosidase may be added to the crude enzyme product. As a heterogenous β-glucosidase, β-glucosidase from the genus *Aspergillus* can be preferably used. As β-glucosidase from the genus *Aspergillus*, Novozyme 188 commercially available from Novozymes and the like can be exemplified. It is also possible to use a culture solution in which β-glucosidase activity is improved by introducing a gene into a microorganism of the genus *Trichoderma* and culturing the microorganism of *Trichoderma* genetically modified to produce β-glucosidase in the culture solution.

The temperature of hydrolysis reaction is preferably 40 to 60° C. Especially, when cellulase from the genus *Trichoderma* is used, the temperature is more preferably 45 to 55° C.

The period of hydrolysis reaction is preferably 2 to 200 hours. When the period is less than 2 hours, a sufficient amount of sugar production cannot be obtained in some cases. On the other hand, when the period is more than 200 hours, deactivation of enzymes may proceed, and reusability of the recovered cellulase may be adversely affected in some cases.

Step (3): A Step of Subjecting the Hydrolyzate of Step (2) to Solid-Liquid Separation into a Solution Component and a Hydrolysis Residue, and Filtering the Solution Component Through an Ultrafiltration Membrane and Recovering the Cellulase from Filamentous Fungi as a Non-Permeate, and Optionally Filtering the Cellulase Through a Microfiltration Membrane The hydrolyzate obtained by step (2) can be separated into a sugar solution and a hydrolysis residue by solid-liquid separation. A method of solid-liquid separation includes centrifugation and press filtration, and press filtration is preferable.

Press filtration is preferable as solid-liquid separation since a clear filtrate can be obtained. Since the solution component recovered by solid-liquid separation is filtrated through an ultrafiltration membrane in step (3) described below, it is preferable in that the amount of a solid content or a fine particulate component is small, from the viewpoint of membrane fouling. In press filtration, since the amount of a solid content or a fine particulate component is small, press filtration can be preferably used.

Furthermore, when clarity of the solution component is low, it is preferable to completely remove the fine particulate component by filtering the solution component through a microfiltration membrane. The microfiltration membrane described in WO 2010/067785 can be used.

The cellulase component from filamentous fungi and sugar component contained in the recovered solution component are separated by filtration using an ultrafiltration membrane. An ultrafiltration membrane is a membrane with a molecular weight cut-off of 500 to 200,000, and also called as an ultrafiltration membrane or a UF membrane. The pore size on the membrane surface is too small to measure with an electron microscope or the like, and a value which is called as molecular weight cut-off is used as an index for the pore size, instead of the average pore size. Molecular weight cut-off is well-known to one skilled in the art as an index indicating the ultrafiltration membrane performance, as described in The Membrane Society of Japan, Maku-gaku Jikken series Volume III, artificial membrane ver., editing committee/Kimura Shoji, Nakao Shinichi Oya Haruhiko, Nakagawa Tsutomu (1993, KYORITSU SHUPPAN CO., LTD.), P92, as "A graph obtained by plotting the molecular weight of the solute on the horizontal axis and the blocking rate on the vertical axis is called as a molecular weight cut-off curve. The molecular weight with the blocking rate of 90% is referred to as molecular weight cut-off of the membrane."

In separation of the cellulase component from filamentous fungi and the sugar component using an ultrafiltration membrane, the molecular weight cut-off is not specifically limited so long as glucose (molecular weight: 180) and xylose (molecular weight: 150), which are monosaccharides as main components of the sugar solution, can permeate and cellulase from filamentous fungi can be blocked. The molecular weight cut-off is preferably 500 to 50,000. From the viewpoint of separating a foreign substance which exhibits an inhibitory action on the enzyme reaction and the enzyme, the molecular weight cut-off is more preferably 5,000 to 50,000, and further preferably 10,000 to 30,000.

As the materials of an ultrafiltration membrane, polyethersulfone (PES), polysulfone (PS), polyacrylonitrile (PAN), polyvinylidene fluoride (PVDF), regenerated cellulose, cellulose, cellulose ester, sulfonated polysulfone, sulfonated polyethersulfone, polyolefin, polyvinyl alcohol, polymethyl methacrylate, polytetrafluoroethylene and the like can be used. Since regenerated cellulose, cellulose and cellulose ester are degraded by cellulase, it is preferable to use an ultrafiltration membrane of which material is a synthetic polymer such as PES and PVDF.

As ultrafiltration methods, there are dead-end filtration and cross-flow filtration. From the viewpoint of suppression of membrane fouling, it is preferable that the method is cross-flow filtration. As a membrane form of the ultrafiltration membrane to be used, appropriate forms such as flat-sheet membrane type, spiral type, tubular type and hollow fiber type can be used. Concretely, G-5 type, G-10 type, G-20 type, G-50 type, PW type and HWSUF type of DESAL, HFM-180, HFM-183, HFM-251, HFM-300, HFK-131, HFK-328, MPT-U20, MPS-U20P and MPS-U20S of Koch Filter Corporation, SPE1, SPE3, SPE5, SPE10, SPE30, SPV5, SPV50 and SOW30 of Synder Filtration, Microza (trademark) UF series corresponding to molecular weight cut-off of 3,000 to 10,000 manufactured by Asahi Kasei Corporation, NTR 7410 and NTR 7450 manufactured by Nitto Denko Corporation, and the like are included.

The hydrolyzate of cellulose-containing biomass contains water-insoluble fine particulates such as lignin, silica, a calcium salt, an aggregate protein and undegraded cellulose; or water-soluble polymers such as an oligosaccharide, a polysaccharide, tannin and a protein; and low molecular weight fermentation inhibitors; an inorganic salt; and an organic acid, and the like as an impurity, in addition to sugar. The ultrafiltration membrane and/or microfiltration membrane generates clogging due to adhesion of such impurities, especially a water-soluble polymer, as operating for a long period. Then, by the following step (4), the clogging component adhered to the separation membrane can be removed, and efficiency of filtration can be maintained. A wash solution containing the clogging component of the separation membrane is recovered and used for the subsequent sugar solution production processes.

Step (4): A Step of Washing the Separation Membrane after Recovering Sugar Solution in Step (3)

Step (4) may be carried out every time in the sugar solution production processes or may be carried out whenever the filtration performance decreased after steps (1) to (3) were repeated some times. Frequent washing has high washing effect and enables a long-lasting separation membrane, but is disadvantageous in terms of washing cost. Since the manner of adhesion of impurities which cause clogging to the separation membrane differs depending on the kind of the separation membrane and cellulose-containing biomass, it is preferable to carry out washing with optimum frequency in each process.

Washing of the separation membrane can be carried out by a known method. There are a method of immersing the separation membrane to a solution to be used for washing (hereinafter referred to as washing water), a method of filtering the whole amount of washing water by the separation membrane, a method of cross-flow filtration of washing water by the separation membrane, and the like, and any method may be used.

In addition to water, a washing water containing an acidic substance such as hydrochloric acid, sulfuric acid, oxalic acid and citric acid (hereinafter referred to as an acidic washing water); a washing water containing an alkaline substance such as sodium hydroxide, calcium hydroxide, triethanolamine, diethanolamine and monoethanolamine (hereinafter referred to as an alkaline washing water); or a chemical liquid containing a known washing agent such as sodium hypochloride and a surfactant may be used as the washing water, and the washing effect can be increased by use of these washing agents. These washing agents may be combined, and washing may be repeated plural times using one, or two or more kinds of washing waters. Since a wash solution of the separation membrane is used for the subsequent sugar solution production processes, it is preferable not to use a washing agent or to use an acidic washing water or an alkaline washing water, from the viewpoint that hydrolysis reaction of cellulose by cellulase from filamentous fungi is difficult to be inhibited. Since it can be thought that most of the impurities which adhere to the separation membrane are organic matters, an alkaline washing water is further preferable, from the viewpoint that the washing water is excellent in washing of an organic matter.

The temperature of the washing water is not specifically limited, however, preferably 0 to 90° C. When the washing temperature is too low, the washing effect may be insufficient in some cases. On the other hand, although the higher the temperature is, the more excellent the washing effect is, the separation membrane itself may be damaged by heat in some cases when the temperature is higher than 90° C., and the filtration performance may decrease. Thus, the temperature of the washing water is preferably 20 to 90° C., and further preferably 40 to 90° C.

As described above, the wash solution obtained in step (4) contains water-insoluble fine particulates such as lignin, silica, a calcium salt, an aggregate protein and undegraded cellulose; or water-soluble polymers such as an oligosaccharide, a polysaccharide, tannin and a protein; and a low molecular weight fermentation inhibitory substance; an inorganic salt; and an organic acid, and the like. Among them, a polymer component which does not pass through a microfiltration membrane and/or an ultrafiltration membrane suppresses adhesion of cellulase from filamentous fungi to hydrolysis residue of cellulose-containing biomass and exhibits a high effect.

When the wash solution is used for step (1) of the subsequent sugar solution production processes, the amount to be used is not specifically limited. However, when the amount to be used is too small, the effect may not be sufficiently obtained in some cases. In addition, when the amount to be used is too large, impurities in the hydrolyzate increases, and the burden on the separation membrane may be increased in some cases. Thus, the amount of the wash solution to be used in step (1) is preferably an amount obtained by repeating sugar solution production processes once to 20 times. Further preferably, the amount is an amount obtained by repeating the process 5 to 10 times.

By growing a microorganism having an ability to produce a chemical using a sugar solution obtained by our methods as a raw material for fermentation, various chemicals can be produced. Growing a microorganism using the sugar solution as a raw material for fermentation herein means utilizing a sugar component or an amino source contained in the sugar solution as a nutrient of the microorganism for proliferation, growing and maintenance of the microorganisms. A concrete example of the chemical includes a substance produced in a large amount in fermentation industry such as alcohol, an organic acid, an amino acid and a nucleic acid. Such chemicals are produced as a chemical using the sugar component in the sugar solution as a carbon source and accumulated in and outside the living body in the course of fermentation thereof. Concrete examples of a chemical which can be produced by a microorganism include an alcohol such as ethanol, 1,3-propanediol, 1,4-butanediol and glycerol; an organic acid such as acidic acid, lactic acid, pyruvic acid, succinic acid, malic acid, itaconic acid and citric acid; a nucleoside such as inosine and guanosine; a nucleotide such as inosinic acid and guanylic acid; and an amine compound such as cadaverine. Furthermore, it is also possible to apply our sugar solution for production of an enzyme, an antibiotic, a recombinant protein and the like. Microorganisms used for production of such chemicals may be any microorganism so long as the microorganism can efficiently produce a chemical of interest, and microorganisms such as *Escherichia coli*, yeast, filamentous fungi, basidomycetes can be used.

EXAMPLES

Our methods will be further concretely described below by Examples. However, this disclosure is not limited thereto.

Reference Example 1

Pretreatment of Cellulose-Containing Biomass

One point eight kilograms (1.8 kg) of cellulose-containing biomass (corn cob) was immersed to 4.2 kg of 1% aqueous sulfuric acid solution and treated by an autoclave (manufactured by NITTO KOATSU CHEMICAL INDUSTRIES, LTD.) at 150° C. for 30 minutes, and used for the following Examples. The moisture content of the material treated by dilute sulfuric acid was 70%.

Reference Example 2

Determination of β-Glucosidase Activity

β-glucosidase activity was used as an index of the recovery efficiency of cellulase from filamentous fungi. The activity was determined and evaluated by the method described below.

To 0.9 mL of a 55 mM acetic acid buffer (pH 5.0) containing 1.1 mM 4-nitrophenyl-β-D-glucopyranoside, 0.1 mL of enzyme solution was added, and a reaction was carried out at 30° C. (final concentration of the substrate: 1 mM, final concentration of the buffer: 50 mM). After carrying out the reaction accurately for 10 minutes, 0.1 mL of 2 M aqueous sodium carbonate solution was added thereto to stop the reaction, and absorbance at 405 nm was determined (OD test). As a blank, absorbance at 405 nm of a substrate solution to which 2 M aqueous sodium carbonate solution and an enzyme solution were added in this order was similarly determined (OD blank). In the above-mentioned reaction system, the amount of enzyme which produces 1 µmol per minute of 4-nitrophenyl was defined as 1 U, and the activity value (U/mL) was calculated according to the following formula. The millimole molecular extinction coefficient of 4-nitrophenol in the above-mentioned reaction system is 17.2 L/mmol/cm.

β-glucosidase activity (U/mL)={(OD test−OD blank)×1.1 (mL)×dilution rate of the enzyme}/ {17.2×10 (minutes)×0.1 (mL)}.

Reference Example 3

Production of a Sugar Solution Using an Ultrafiltration Membrane and a Microfiltration Membrane Step 1: Preparation of Slurry of Pretreated Cellulose-Containing Biomass Four kilograms (4 kg) of the product from the dilute sulfuric acid treated cellulose-containing biomass (corn cob) of Reference Example 1 was suspended in water to prepare slurry, and a 10% aqueous ammonium solution was added thereto, to adjust the pH to 5.0. Thereafter, water was added thereto to make up the gross weight to 8 kg, and the solid concentration of the slurry was adjusted to 15%.

Step 2: Hydrolysis of Slurry of Pretreated Cellulose-Containing Biomass

To the slurry prepared in step 1, 240 mL of commercially available enzyme solution ("ACCELLERASE (trademark) DUET", manufactured by Genencor International, Inc.) was added, and the reaction carried out at 50° C. for 24 hours.

Step 3: Recovery of Cellulase and a Sugar Solution from Hydrolyzate of Cellulose-Containing Biomass The hydrolyzate of step 2 was filtered by a filter press apparatus (manufactured by YABUTA Industries, Co., Ltd, MO-4), and insoluble particulates of micron order were removed by subjecting the solution component to a microfiltration membrane having average pore size of 0.04 um (manufactured by DESAL, E series, material: polysulfone). As a membrane separation apparatus, a small-scale flat-sheet membrane unit "Sepa (trademark) CF-II" (manufactured by GE, effective membrane area: 140 cm$^2$) which can be used as a filtration small scale test of a spiral membrane module was used. The operation temperature was 25° C., and the membrane surface linear speed was 20 cm/sec. Five liters (5 L) of filtrate was obtained, and subjected to filtration by an ultrafiltration membrane.

As an ultrafiltration membrane, a heat-resistant ultrafiltration membrane (manufactured by DESAL, "HWSUF" series) was used. As a membrane separation apparatus, "Sepa (trademark) CF-II" (manufactured by GE, effective membrane area: 140 cm$^2$) was used. The operation temperature was 25° C., and the membrane surface linear speed was 20 cm/sec. Controlling the operation pressure so that the membrane flux was constant at 0.1 m/D, 4 L out of 5 L were filtrated. The filtrate was recovered as a sugar solution, and the non-permeate was recovered as a recovered cellulase solution, respectively.

Step 4: Washing the Separation Membranes

The microfiltration membrane and the ultrafiltration membrane used in step 3 were washed using a 0.0125 M aqueous sodium hydroxide solution as washing water. First, cross-flow filtration was carried out using 2 L of washing water, at washing water temperature of 25° C., at operation pressure of 0.1 MPa, and at the membrane surface linear speed of 30 cm/sec, and the filtrate was recovered as wash solution 1 of the separation membrane. Next, membrane washing was carried out using another 2 L of washing water, under the same operation conditions and by circulating the cross-flow for 20 minutes. After 20 minutes, the circulated solution was recovered as wash solution 2 of the separation membrane. The membrane separation apparatus was the same one as that used in step 3.

Comparative Example 1

Use of Unused Washing Water

As washing water, 2 L of unused 0.0125 M aqueous sodium hydroxide solution was used in step 1, to prepare slurry of a pretreated material. Since the solid concentration of the slurry could not be adjusted to 15% only by 2 L of aqueous sodium hydroxide solution, water was added thereto to supply the shortage. By the method described in Reference Example 3 in terms of other conditions, a recovered cellulase solution was obtained, and activity determination was carried out according to Reference Example 2.

Example 1

Use of Wash Solution of the Separation Membranes

After repeating steps 1 to 3 of the sugar solution production processes of Reference Example 3 five times, the separation membrane was washed by the same method as in step 4, and wash solution 1 of the separation membrane and wash solution 2 of the separation membrane were combined and recovered as wash solution 1+2 of the separation membrane. After repeating steps 1 to 3 another five times, the separation membrane was washed, and wash solution 1 of the separation membrane and wash solution 2 of the separation membrane were separately recovered. The whole amount of each recovered wash solution of the separation membrane was used in step 1, to prepare slurry of a pretreated material. Since the solid concentration of the slurry could not be adjusted to 15% only by the wash solution of the separation membrane, water was added thereto to supply the shortage. By the method described in Reference Example 3 in terms of other conditions, a recovered cellulase solution was obtained, and activity determination was carried out according to Reference Example 2. The results are shown in Table 1 as relative activity. Even when wash solution 1, 2, and 1+2 of the separation membrane of the microfiltration membrane and the ultrafiltration membrane were used, the activity of the recovered cellulase solution greatly increased, and a remarkable effect was obtained especially when wash solution 2 of the separation membrane of the microfiltration membrane and the ultrafiltration membrane was contained.

TABLE 1

| | Preparation of slurry | Relative activity of recovered cellulase solution |
|---|---|---|
| Comparative Example 1 | Aqueous sodium hydroxide solution | 1.0 (Baseline) |
| Example 1 | Wash solution 1 of microfiltration membrane | 17 |
| | Wash solution 2 of microfiltration membrane | 48 |
| | Wash solution 1 + 2 of microfiltration membrane | 47 |
| | Wash solution 1 of ultrafiltration membrane | 10 |
| | Wash solution 2 of ultrafiltration membrane | 32 |

TABLE 1-continued

| Preparation of slurry | Relative activity of recovered cellulase solution |
|---|---|
| Wash solution 1 + 2 of ultrafiltration membrane | 33 |

Example 2

Frequency of washing of separation membrane and cellulase recovery effect

After repeatedly carrying out steps 1 to 3 of the sugar solution production process of Reference Example 3 1, 2, 3, 5, or 10 times, the separation membrane was washed by the same manner as in step 4. In all of the present Examples, wash solution 1 of the separation membrane and wash solution 2 of the separation membrane were combined, and respectively recovered as wash solution 1+2 of the separation membrane. The recovered wash solution 1+2 of the separation membrane was used in step 1 in the same manner as in Example 1, and a recovered cellulase solution was obtained. Activity determination of the recovered cellulase solution was carried out according to Reference Example 2, and the results are shown in Table 2 as relative activity. There was a tendency that the more times steps 1 to 3 were repeated before carrying out washing of the separation membrane, the more the activity of the recovered cellulase solution increased.

TABLE 2

| | Frequency of carrying out steps 1 to 3 | Preparation of slurry | Relative activity of recovered cellulase solution |
|---|---|---|---|
| Comparative Example 1 | — | Aqueous sodium hydroxide solution | 1.0 (Baseline) |
| Example 2 | 1 | Wash solution of microfiltration membrane | 8.3 |
| | | Wash solution of ultrafiltration membrane | 6.9 |
| | 2 | Wash solution of microfiltration membrane | 12 |
| | | Wash solution of ultrafiltration membrane | 11 |
| | 3 | Wash solution of microfiltration membrane | 27 |
| | | Wash solution of ultrafiltration membrane | 23 |
| | 5 | Wash solution of microfiltration membrane | 47 |
| | | Wash solution of ultrafiltration membrane | 33 |
| | 10 | Wash solution of microfiltration membrane | 61 |
| | | Wash solution of ultrafiltration membrane | 46 |

INDUSTRIAL APPLICABILITY

Our sugar solution can be used as a sugar raw material for a wide variety of fermentation products.

The invention claimed is:

1. A method of producing a sugar solution by repeating a sugar solution production process comprising steps (1) to (4):
    step (1): preparing a slurry of a pretreated cellulose-containing biomass;
    step (2): hydrolyzing the slurry of pretreated cellulose-containing biomass in step (1) using a cellulase from filamentous fungi;
    step (3): subjecting a hydrolyzate of step (2) to solid-liquid separation into a solution component and a hydrolysis residue, filtering the solution component through a microfiltration membrane and an ultrafiltration membrane in order and recovering the cellulase from filamentous fungi as a non-permeate, and recovering the sugar solution as a permeate; and
    step (4): washing separation membranes used in step (3) after repeating steps (1) to (3) for at least five times, and recovering a wash solution containing a polymer component that does not pass through one or both of a microfiltration membrane and an ultrafiltration membrane, and using the recovered microfiltration membrane wash solution for step (1) of a subsequent sugar solution production process.

2. The method according to claim 1, wherein the wash solution obtained by washing the microfiltration membrane and ultrafiltration membrane in step (4) is used in step (1) of the subsequent sugar solution production process.

3. The method according to claim 1, step (4) further comprising a separation membrane used in step (3), washing with washing water containing an alkaline substance.

4. The method according to claim 1, wherein the cellulase from filamentous fungi is derived from a microorganism of the genus *Trichoderma*.

5. The method according to claim 1, wherein pretreatment of the cellulose-containing biomass in step (1) is dilute sulfuric acid treatment.

6. The method according to claim 2, further comprising a step (4) comprising a separation membrane used in step (3), washing with washing water containing an alkaline substance.

7. The method according to claim 2, wherein the cellulase from filamentous fungi is derived from a microorganism of the genus *Trichoderma*.

8. The method according to claim 3, wherein the cellulase from filamentous fungi is derived from a microorganism of the genus *Trichoderma*.

9. The method according to claim 2, wherein pretreatment of the cellulose-containing biomass in step (1) is dilute sulfuric acid treatment.

10. The method according to claim 3, wherein pretreatment of the cellulose-containing biomass in step (1) is dilute sulfuric acid treatment.

11. The method according to claim 4, wherein pretreatment of the cellulose-containing biomass in step (1) is dilute sulfuric acid treatment.

* * * * *